(12) United States Patent
Horvath et al.

(10) Patent No.: US 7,459,568 B2
(45) Date of Patent: Dec. 2, 2008

(54) ALPHA CRYSTALLINE FORM OF STRONTIUM RANELATE

(75) Inventors: Stéphane Horvath, La Chapelle Saint Mesmin (FR); Isabelle Demuynck, Orleans (FR); Gérard Damien, Meung sur Loire (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 467 days.

(21) Appl. No.: 11/140,822

(22) Filed: May 31, 2005

(65) Prior Publication Data

US 2006/0069271 A1 Mar. 30, 2006

(30) Foreign Application Priority Data

Sep. 30, 2004 (FR) .................................. 04 10335

(51) Int. Cl.
*A61K 31/381* (2006.01)
*C07D 333/36* (2006.01)

(52) U.S. Cl. .............................. 549/61; 514/61; 549/447

(58) Field of Classification Search .................... 549/3, 549/61; 514/184, 447
See application file for complete search history.

(56) References Cited

U.S. PATENT DOCUMENTS

2004/0059134 A1  3/2004  Vaysse-Ludot et al.
2004/0059135 A1  3/2004  Vaysse-Ludot et al.

FOREIGN PATENT DOCUMENTS

EP  0415850  3/1991
EP  0693285  1/1996
EP  0813869  12/1997
FR  0415850 A1 *  8/1990
FR  2844795  3/2004
RU  2149631  5/2000
WO  WO 98/16521  4/1998
WO  WO 2004/029036  4/2004

OTHER PUBLICATIONS

*Eurasian Search Report for Eurasian Application No. 200500842*, Jun. 17, 2005.
*French Search Report for French Application No. 04.10335*, Apr. 22, 2005.
*International Search Report for International Application No. PCT/FR2005/001515*, Nov. 28, 2005.
Sorbera, et al., *Drugs of the Future*, 2003, 28, 328-335.
Reginster, et al., *Drugs of Today*, 2003, 39, 89-101.

\* cited by examiner

*Primary Examiner*—Kamal Saeed
*Assistant Examiner*—Janet L Coppins
(74) *Attorney, Agent, or Firm*—Hueschen and Sage

(57) ABSTRACT

Alpha crystalline form of strontium ranelate of formula (I):

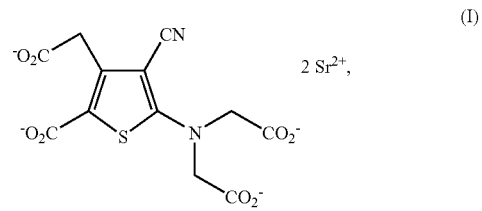

characterized by its powder X-ray diffraction diagram and by a water content of from 22 to 24%.

Medicinal products containing the same which are useful in the treatment of osteoporosis and arthrosis.

5 Claims, No Drawings

ALPHA CRYSTALLINE FORM OF STRONTIUM RANELATE

The present invention relates to the alpha crystalline form of strontium ranelate.

BACKGROUND OF THE INVENTION

Strontium ranelate, represented by formula (I):

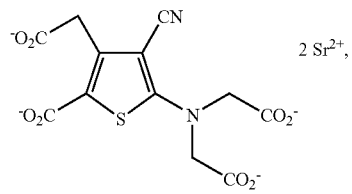

or the distrontium salt of 5-[bis(carboxymethyl)amino]-3-carboxymethyl-4-cyano-2-thiophenecarboxylic acid, and its hydrates have very valuable pharmacological and therapeutic properties, especially pronounced anti-osteoporotic properties, making these compounds useful in the treatment and prevention of bone diseases.

Strontium ranelate and its hydrates also have properties making them useful in the treatment and prevention of arthrosis.

DESCRIPTION OF THE PRIOR ART

The preparation and therapeutic use of strontium ranelate and its tetrahydrate, heptahydrate and octahydrate have been described in the European Patent Specification EP 0 415 850.

The use of strontium ranelate in the prevention and treatment of arthrosis has been described in the European Patent Specification EP 0 813 869.

DETAILED DESCRIPTION OF THE INVENTION

The Applicant has now found that strontium ranelate can be obtained in a well-defined crystalline form which is perfectly reproducible and which, by virtue of that fact, has valuable characteristics in terms of filtration and ease of formulation.

More specifically, the present invention relates to the alpha crystalline form of strontium ranelate, characterised by a water content of from 22 to 24% and by the following powder X-ray diffraction diagram measured using a PANalytical X'Pert Pro diffractometer together with an X'Celerator detector and expressed in terms of ray position (Bragg's angle 2 theta, expressed in degrees), ray height (expressed in counts), ray area (expressed in counts×degrees), ray width at half-height ("FWHM", expressed in degrees) and interplanar distance d (expressed in Å)

| Ray no. | Angle 2 theta (degrees) | Height (counts) | Area (counts × degrees) | FWHM (degrees) | Interplanar distance (Å) |
|---|---|---|---|---|---|
| 1 | 7.6 | 4527 | 448 | 0.1004 | 11.649 |
| 2 | 8.0 | 1438 | 142 | 0.1004 | 11.069 |
| 3 | 8.3 | 3522 | 349 | 0.1004 | 10.642 |
| 4 | 8.6 | 11347 | 1123 | 0.1004 | 10.272 |
| 5 | 8.9 | 7332 | 726 | 0.1004 | 9.889 |
| 6 | 11.0 | 1047 | 104 | 0.1004 | 8.072 |
| 7 | 11.3 | 1655 | 164 | 0.1004 | 7.840 |
| 8 | 12.0 | 2186 | 216 | 0.1004 | 7.355 |
| 9 | 13.2 | 2887 | 381 | 0.1338 | 6.703 |
| 10 | 13.5 | 1705 | 169 | 0.1004 | 6.557 |
| 11 | 14.1 | 154 | 30 | 0.2007 | 6.275 |
| 12 | 14.7 | 803 | 79 | 0.1004 | 6.035 |
| 13 | 14.9 | 1346 | 178 | 0.1338 | 5.942 |
| 14 | 15.8 | 1556 | 154 | 0.1004 | 5.613 |
| 15 | 16.0 | 3339 | 441 | 0.1338 | 5.527 |
| 16 | 16.7 | 1845 | 183 | 0.1004 | 5.308 |
| 17 | 17.3 | 2835 | 281 | 0.1004 | 5.127 |
| 18 | 17.6 | 1252 | 124 | 0.1004 | 5.049 |
| 19 | 18.0 | 2183 | 216 | 0.1004 | 4.939 |
| 20 | 19.2 | 2303 | 228 | 0.1004 | 4.622 |
| 21 | 19.8 | 1298 | 128 | 0.1004 | 4.475 |
| 22 | 20.3 | 788 | 78 | 0.1004 | 4.373 |
| 23 | 20.6 | 1039 | 103 | 0.1004 | 4.317 |
| 24 | 21.1 | 882 | 116 | 0.1338 | 4.211 |
| 25 | 21.7 | 390 | 38 | 0.1004 | 4.103 |
| 26 | 22.3 | 1919 | 253 | 0.1338 | 3.990 |
| 27 | 22.7 | 1805 | 179 | 0.1004 | 3.923 |
| 28 | 23.0 | 4043 | 467 | 0.1171 | 3.861 |
| 29 | 23.5 | 650 | 86 | 0.1338 | 3.792 |
| 30 | 24.0 | 8677 | 1002 | 0.1171 | 3.711 |
| 31 | 24.7 | 229 | 30 | 0.1338 | 3.600 |
| 32 | 25.1 | 1246 | 164 | 0.1338 | 3.543 |
| 33 | 25.6 | 1659 | 219 | 0.1338 | 3.473 |
| 34 | 25.9 | 1773 | 175 | 0.1004 | 3.442 |
| 35 | 26.3 | 695 | 69 | 0.1004 | 3.385 |
| 36 | 26.6 | 401 | 46 | 0.1171 | 3.355 |
| 37 | 27.0 | 2800 | 370 | 0.1338 | 3.300 |
| 38 | 27.6 | 1415 | 140 | 0.1004 | 3.230 |
| 39 | 28.0 | 3250 | 429 | 0.1338 | 3.186 |
| 40 | 28.4 | 1513 | 250 | 0.1673 | 3.144 |
| 41 | 29.1 | 1456 | 144 | 0.1004 | 3.068 |
| 42 | 29.6 | 1943 | 192 | 0.1004 | 3.022 |
| 43 | 30.1 | 3637 | 540 | 0.1506 | 2.967 |
| 44 | 30.5 | 707 | 117 | 0.1673 | 2.929 |
| 45 | 30.9 | 596 | 59 | 0.1004 | 2.897 |
| 46 | 31.8 | 577 | 76 | 0.1338 | 2.816 |
| 47 | 32.0 | 1080 | 107 | 0.1004 | 2.796 |
| 48 | 32.5 | 512 | 51 | 0.1004 | 2.756 |
| 49 | 32.9 | 1268 | 167 | 0.1338 | 2.726 |
| 50 | 33.4 | 1180 | 117 | 0.1004 | 2.685 |

The invention relates also to a process for the preparation of the alpha crystalline form of strontium ranelate, characterised in that a solution of strontium ranelate or a hydrate thereof in water is heated to reflux and then cooled until crystallisation is complete, and the product is collected by filtration.

In the preparation process according to the invention it is possible to use strontium ranelate or a hydrate thereof obtained by any process, for example strontium ranelate octahydrate obtained by the preparation process described in the Patent Specification EP 0 415 850.

An advantage of obtaining the said crystalline form is to allow especially rapid and efficient filtration and also the preparation of pharmaceutical formulations of consistent and reproducible composition, which is especially advantageous when the formulations are intended for oral administration.

The form thereby obtained is sufficiently stable to allow its storage for an extended period without particular conditions in terms of temperature, light, humidity or oxygen levels.

The invention relates also to pharmaceutical compositions comprising as active ingredient the alpha crystalline form of strontium ranelate together with one or more appropriate, inert and non-toxic excipients. Among the pharmaceutical compositions according to the invention there may be mentioned, more especially, those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The useful dosage can be varied according to the nature and severity of the disorder, the administration route and the age and weight of the patient. The dosage varies from 0.2 to 10 g per day in one or more administrations.

The Examples that follow illustrate the invention.

The X-ray powder diffraction spectrum was measured under the following experimental conditions:
PANalytical X'Pert Pro diffractometer, X'Celerator detector,
voltage 45 kV, intensity 40 mA,
mounting θ-θ,
Kβ (Ni) filter,
incident-beam and diffracted-beam Soller slit: 0.04 rad,
divergence slits: automatic, irradiated length: 10 mm,
mask: 10 mm,
antiscatter slit: ½°,
measurement mode: continuous from 3° to 34°, in increments of 0.017°,
measurement time per step: 31.1 s,
total time: 8 min 07 s,
measurement speed: 0.068°/s,
spinner: turning at 1 revolution/s,
measurement temperature: ambient.

EXAMPLE 1

Alpha Crystalline Form of Strontium Ranelate 200 g of strontium ranelate octahydrate obtained according to the process described in Patent Specification EP 0 415 850 are mixed with 2 litres of water and heated to reflux.

The mixture is then cooled to 20° C.

The solid obtained is collected by filtration.

The water content of the product obtained, determined by loss on drying, is from 22 to 24%, which corresponds to from 8.1 to 9 molecules of water per molecule of strontium ranelate.

X-Ray Powder Diffraction Diagram:

The X-ray powder diffraction profile (diffraction angles) of the alpha form of strontium ranelate is given by the significant rays collated in the following table:

| Ray no. | Angle 2 theta (degrees) | Height (counts) | Area (counts × degrees) | FWHM (degrees) | Interplanar distance (Å) |
|---|---|---|---|---|---|
| 1 | 7.6 | 4527 | 448 | 0.1004 | 11.649 |
| 2 | 8.0 | 1438 | 142 | 0.1004 | 11.069 |
| 3 | 8.3 | 3522 | 349 | 0.1004 | 10.642 |
| 4 | 8.6 | 11347 | 1123 | 0.1004 | 10.272 |
| 5 | 8.9 | 7332 | 726 | 0.1004 | 9.889 |
| 6 | 11.0 | 1047 | 104 | 0.1004 | 8.072 |
| 7 | 11.3 | 1655 | 164 | 0.1004 | 7.840 |
| 8 | 12.0 | 2186 | 216 | 0.1004 | 7.355 |
| 9 | 13.2 | 2887 | 381 | 0.1338 | 6.703 |
| 10 | 13.5 | 1705 | 169 | 0.1004 | 6.557 |
| 11 | 14.1 | 154 | 30 | 0.2007 | 6.275 |
| 12 | 14.7 | 803 | 79 | 0.1004 | 6.035 |
| 13 | 14.9 | 1346 | 178 | 0.1338 | 5.942 |
| 14 | 15.8 | 1556 | 154 | 0.1004 | 5.613 |
| 15 | 16.0 | 3339 | 441 | 0.1338 | 5.527 |
| 16 | 16.7 | 1845 | 183 | 0.1004 | 5.308 |
| 17 | 17.3 | 2835 | 281 | 0.1004 | 5.127 |
| 18 | 17.6 | 1252 | 124 | 0.1004 | 5.049 |
| 19 | 18.0 | 2183 | 216 | 0.1004 | 4.939 |
| 20 | 19.2 | 2303 | 228 | 0.1004 | 4.622 |
| 21 | 19.8 | 1298 | 128 | 0.1004 | 4.475 |
| 22 | 20.3 | 788 | 78 | 0.1004 | 4.373 |
| 23 | 20.6 | 1039 | 103 | 0.1004 | 4.317 |
| 24 | 21.1 | 882 | 116 | 0.1338 | 4.211 |
| 25 | 21.7 | 390 | 38 | 0.1004 | 4.103 |
| 26 | 22.3 | 1919 | 253 | 0.1338 | 3.990 |
| 27 | 22.7 | 1805 | 179 | 0.1004 | 3.923 |
| 28 | 23.0 | 4043 | 467 | 0.1171 | 3.861 |
| 29 | 23.5 | 650 | 86 | 0.1338 | 3.792 |
| 30 | 24.0 | 8677 | 1002 | 0.1171 | 3.711 |
| 31 | 24.7 | 229 | 30 | 0.1338 | 3.600 |
| 32 | 25.1 | 1246 | 164 | 0.1338 | 3.543 |
| 33 | 25.6 | 1659 | 219 | 0.1338 | 3.473 |
| 34 | 25.9 | 1773 | 175 | 0.1004 | 3.442 |
| 35 | 26.3 | 695 | 69 | 0.1004 | 3.385 |
| 36 | 26.6 | 401 | 46 | 0.1171 | 3.355 |
| 37 | 27.0 | 2800 | 370 | 0.1338 | 3.300 |
| 38 | 27.6 | 1415 | 140 | 0.1004 | 3.230 |
| 39 | 28.0 | 3250 | 429 | 0.1338 | 3.186 |
| 40 | 28.4 | 1513 | 250 | 0.1673 | 3.144 |
| 41 | 29.1 | 1456 | 144 | 0.1004 | 3.068 |
| 42 | 29.6 | 1943 | 192 | 0.1004 | 3.022 |
| 43 | 30.1 | 3637 | 540 | 0.1506 | 2.967 |
| 44 | 30.5 | 707 | 117 | 0.1673 | 2.929 |
| 45 | 30.9 | 596 | 59 | 0.1004 | 2.897 |
| 46 | 31.8 | 577 | 76 | 0.1338 | 2.816 |
| 47 | 32.0 | 1080 | 107 | 0.1004 | 2.796 |
| 48 | 32.5 | 512 | 51 | 0.1004 | 2.756 |
| 49 | 32.9 | 1268 | 167 | 0.1338 | 2.726 |
| 50 | 33.4 | 1180 | 117 | 0.1004 | 2.685 |

EXAMPLE 2

Pharmaceutical Composition

Formula for the preparation of 1000 tablets each containing 0.5 g of active ingredient:

| | |
|---|---|
| Compound of Example 1 | 658 g |
| Sodium carboxymethyl starch | 25.5 g |
| Microcrystalline cellulose | 119.4 g |
| Povidone | 38 g |
| Anhydrous colloidal silica | 1.5 g |
| Magnesium stearate | 7.6 g |

We claim:

1. The alpha crystalline form of the compound of formula (I):

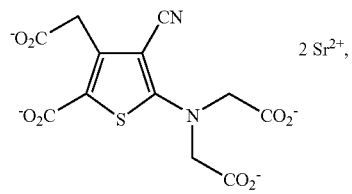

2 Sr²⁺,     (I)

wherein the compound has a water content of from 22 to 24% and exhibits essentially the following powder X-ray diffraction diagram expressed in terms of ray position (Bragg's angle 2 theta, expressed in degrees), ray height (expressed in counts), ray area (expressed in counts×degrees), ray width at half-height ("FWHM", expressed in degrees) and interplanar distance d (expressed in Å):

| Ray no. | Angle 2 theta (degrees) | Height (counts) | Surface (counts × degrees) | FWHM (degrees) | Interplanar distance (Å) |
|---|---|---|---|---|---|
| 1 | 7.6 | 4527 | 448 | 0.1004 | 11.649 |
| 2 | 8.0 | 1438 | 142 | 0.1004 | 11.069 |
| 3 | 8.3 | 3522 | 349 | 0.1004 | 10.642 |
| 4 | 8.6 | 11347 | 1123 | 0.1004 | 10.272 |
| 5 | 8.9 | 7332 | 726 | 0.1004 | 9.889 |
| 6 | 11.0 | 1047 | 104 | 0.1004 | 8.072 |
| 7 | 11.3 | 1655 | 164 | 0.1004 | 7.840 |
| 8 | 12.0 | 2186 | 216 | 0.1004 | 7.355 |
| 9 | 13.2 | 2887 | 381 | 0.1338 | 6.703 |
| 10 | 13.5 | 1705 | 169 | 0.1004 | 6.557 |
| 11 | 14.1 | 154 | 30 | 0.2007 | 6.275 |
| 12 | 14.7 | 803 | 79 | 0.1004 | 6.035 |
| 13 | 14.9 | 1346 | 178 | 0.1338 | 5.942 |
| 14 | 15.8 | 1556 | 154 | 0.1004 | 5.613 |
| 15 | 16.0 | 3339 | 441 | 0.1338 | 5.527 |
| 16 | 16.7 | 1845 | 183 | 0.1004 | 5.308 |
| 17 | 17.3 | 2835 | 281 | 0.1004 | 5.127 |
| 18 | 17.6 | 1252 | 124 | 0.1004 | 5.049 |
| 19 | 18.0 | 2183 | 216 | 0.1004 | 4.939 |
| 20 | 19.2 | 2303 | 228 | 0.1004 | 4.622 |
| 21 | 19.8 | 1298 | 128 | 0.1004 | 4.475 |
| 22 | 20.3 | 788 | 78 | 0.1004 | 4.373 |
| 23 | 20.6 | 1039 | 103 | 0.1004 | 4.317 |
| 24 | 21.1 | 882 | 116 | 0.1338 | 4.211 |
| 25 | 21.7 | 390 | 38 | 0.1004 | 4.103 |
| 26 | 22.3 | 1919 | 253 | 0.1338 | 3.990 |
| 27 | 22.7 | 1805 | 179 | 0.1004 | 3.923 |
| 28 | 23.0 | 4043 | 467 | 0.1171 | 3.861 |
| 29 | 23.5 | 650 | 86 | 0.1338 | 3.792 |
| 30 | 24.0 | 8677 | 1002 | 0.1171 | 3.711 |
| 31 | 24.7 | 229 | 30 | 0.1338 | 3.600 |
| 32 | 25.1 | 1246 | 164 | 0.1338 | 3.543 |
| 33 | 25.6 | 1659 | 219 | 0.1338 | 3.473 |
| 34 | 25.9 | 1773 | 175 | 0.1004 | 3.442 |
| 35 | 26.3 | 695 | 69 | 0.1004 | 3.385 |
| 36 | 26.6 | 401 | 46 | 0.1171 | 3.355 |
| 37 | 27.0 | 2800 | 370 | 0.1338 | 3.300 |
| 38 | 27.6 | 1415 | 140 | 0.1004 | 3.230 |
| 39 | 28.0 | 3250 | 429 | 0.1338 | 3.186 |
| 40 | 28.4 | 1513 | 250 | 0.1673 | 3.144 |
| 41 | 29.1 | 1456 | 144 | 0.1004 | 3.068 |
| 42 | 29.6 | 1943 | 192 | 0.1004 | 3.022 |
| 43 | 30.1 | 3637 | 540 | 0.1506 | 2.967 |
| 44 | 30.5 | 707 | 117 | 0.1673 | 2.929 |
| 45 | 30.9 | 596 | 59 | 0.1004 | 2.897 |
| 46 | 31.8 | 577 | 76 | 0.1338 | 2.816 |
| 47 | 32.0 | 1080 | 107 | 0.1004 | 2.796 |
| 48 | 32.5 | 512 | 51 | 0.1004 | 2.756 |
| 49 | 32.9 | 1268 | 167 | 0.1338 | 2.726 |
| 50 | 33.4 | 1180 | 117 | 0.1004 | 2.685. |

2. A process for the preparation of the alpha crystalline form of the compound of claim 1, wherein a solution of strontium ranelate or a hydrate thereof in water is heated at reflux and then cooled until crystallisation is complete, and the product is collected by filtration.

3. A pharmaceutical composition comprising as active ingredient an effective amount of the compound of claim 1 in combination with one or more pharmaceutically acceptable, inert and non-toxic carriers.

4. A method of treating a living animal body, including a human, afflicted with osteoporosis, comprising the step of administering to the living animal body, including a human, an amount of a compound of claim 1 which is effective for alleviation of osteoporosis.

5. A method of treating a living animal body, including a human, afflicted with arthrosis, comprising the step of administering to the living animal body, including a human, an amount of a compound of claim 1 which is effective for alleviation of arthrosis.

* * * * *